July 31, 1973 W. A. WARRINER Plant Pat. 3,381
ROSE PLANT
Filed Oct. 15, 1971
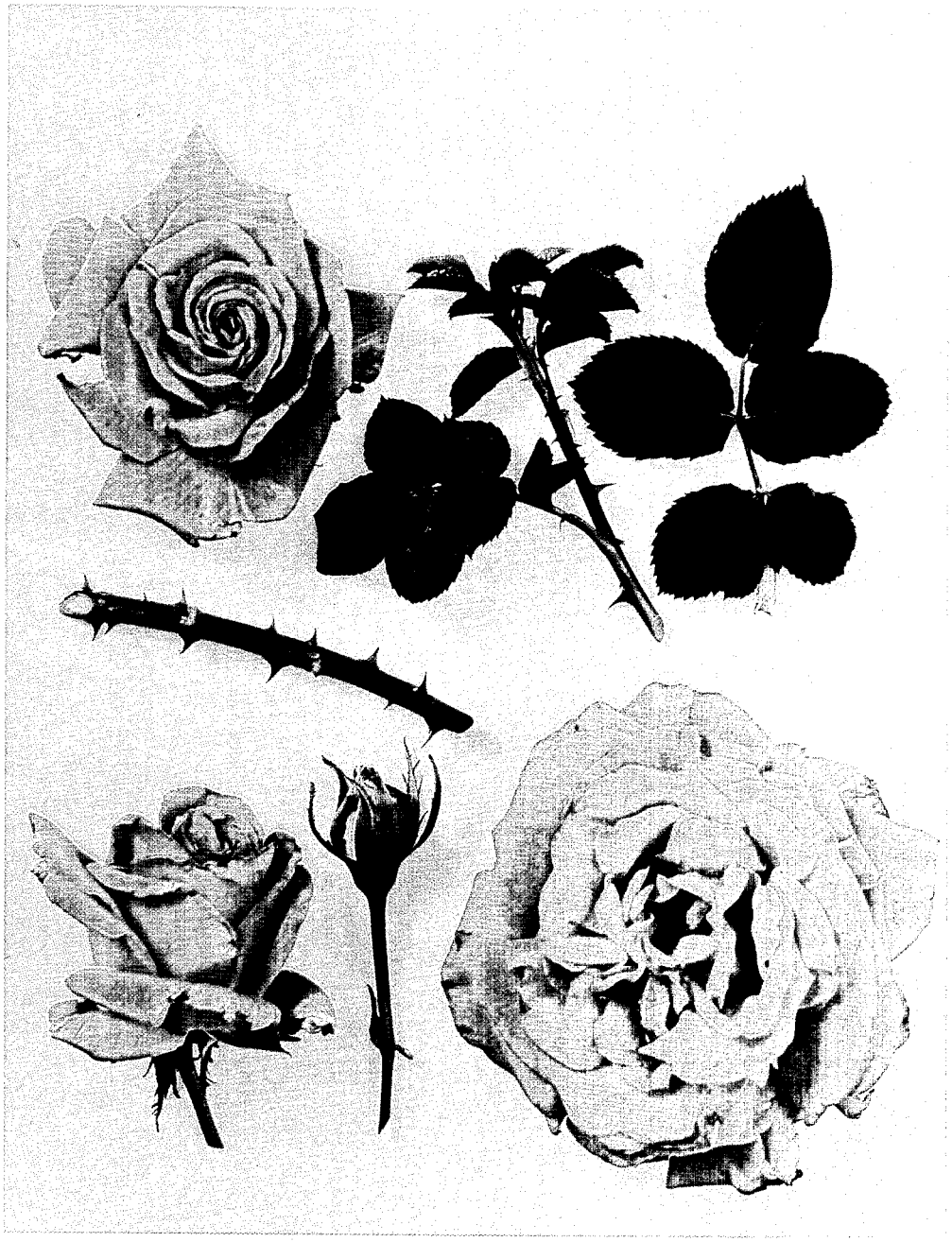
WILLIAM A. WARRINER
INVENTOR
BUCKHORN, BLORE, KLARQUIST & SPARKMAN
ATTORNEYS

United States Patent Office

Plant Pat. 3,381
Patented July 31, 1973

3,381
ROSE PLANT

William A. Warriner, Tustin, Calif., assignor to Jackson & Perkins Company, Medford, Oreg.

Filed Oct. 15, 1971, Ser. No. 189,680
Int. Cl. A01h *5/00*
U.S. Cl. Plt.—20 1 Claim

This invention relates to a new and distinct variety of rose plant of the hybrid tea class originated by me by crossing the variety Fragrant Cloud, U.S. Plant Patent 2,574, by the variety Proud Land, U.S. Plant Patent 2,737.

The primary objective of this breeding was to produce a new and improved variety of the hybrid tea class having a vigorous well branched plant bearing flowers of a near red hue.

This objective was fully achieved along with other desirable improvements as evidenced by the following unique combination of characteristics which are outstanding in the new variety, and which distinguish it from its parents, as well as from all other varieties of which I am aware:

(1) A vigorous, upright and well branched habit of growth.

(2) Abundantly produced blooms of large size very near Cardinal red (Wilson's) in color, aging to Rose Madder.

(3) A very strong resistance to Rose Powdery Mildew (*Sphaerotheca pannosa rosae*) as observed at Irvine, Calif. and Newark, N.Y., such that symptoms of the disease have rarely been seen on plants of this variety.

(4) A slight fragrance.

Asexual reproduction of my new variety by budding as performed at Wasco, Calif. shows that the aforementioned characteristics come true to form and are established and transmitted through succeeding propagations.

The accompanying drawing shows typical specimens of the vegetative growth and flowers of this new variety in different stages of development and as depicted in color as nearly true as it is reasonably possible to make the same in a color illustration of this character.

The following is a detailed description of my new rose variety with color terminology in accordance with Wilson's Horticultural Color Chart, except where ordinary dictionary significance of color is indicated.

Parentage: Seedling.
- *Seed parent.*—Fragrant Cloud, U.S Plant Patent 2,574.
- *Pollen parent.*—Proud Land, U.S. Plant Patent 2,737.

Classification:
- *Botanic.*—Rosa hybrid.
- *Commercial.*—Hybrid tea.

*Flower*

Observations were made at Irvine, Calif. in early September 1971, in the afternoon.

Blooming habit: Recurrent—continuous.

Bud:
- *Size.*—1" to 1¼" when petals start to unfurl.
- *Form.*—Pointed, ovoid.
- *Color.*—When sepals first divide Oxblood Red (00823). When half blown; inside of petals Cardinal Red (822/3); reverse of petals slightly lighter than Cardinal Red (828/3).
- *Sepals.*—Color: Outer surface—Scheeles Green (860) with center area lighter Scheeles Green (860/3). Inner surface—Scheeles Green (860) covered heavily with white pubescence (or tomentum.) Three appendaged sepals normally appendaged. Two unappendaged sepals smooth edged.

- *Receptacle.*—Color: Scheeles Green (860/1). Shape: funnel. Size: Average. Surface: smooth.
- *Peduncle.*—Length: medium. Surface: smooth. Color: Light Green. Strength: stiff, erect.
- *Opening.*—Slowly, outer petals curl back while center is still closed, giving high centered form in half open stage.

Bloom:
- *Size.*—Large. Average size when fully expanded, 4½"–5".
- *Borne.*—Singly, occasionally several together.
- *Stems.*—Medium normal.
- *Form.*—When first open, high center. Permanence—outer petal edges slightly curled, outside edges of outer rows of petals slightly quilled.
- *Petalage.*—30–35 petals under normal conditions.
- *Color.*—Center of flower: upper side of petals lighter than Cardinal Red (822/3) blending to Rose Madder (23) in lower fourth of petal. Reverse side of petals Rose Madder (23). Outer petals: upper side of petals Rose Madder (23). Reverse of petals Rose Madder (23/1). Base of petals—small area on upper side Buttercup Yellow (5/2). General tonality from a distance—fresh open flowers Cardinal Red (822/3). Flowers open several days Rose Madder (23). No variegations.
- *Discoloration.*—General tonality at end of first day—color slowly fades from Cardinal Red (822/3) in buds to Rose Madder (23) to Rose Madder (23/1) when petals fall.
- *Fragrance.*—Slight.

Petals:
- *Texture.*—Moderately thick.
- *Surface.*—Inside—satiny. Reverse—satiny.
- *Shape.*—Very broadly oval.
- *Form.*—Tips slightly recurved; outer petals, edges slightly quilled.
- *Arrangement.*—Informal.
- *Persistence.*—Drop off cleanly.
- *Lastingness.*—On the plant—long. As cut flower—long.

Reproductive parts:
- *Stamens, anthers.*—Small, relatively few. Color—Yellow. Arrangement—regular around styles.
- *Stamens, filaments (threads).*—Medium. Color—yellow at base. Upper portion pink.
- *Pollen.*—Color—gold yellow.
- *Styles.*—Loosely separated, of uneven lengths, thin.
- *Stigmas.*—Color—light yellow.
- *Ovaries.*—All enclosed in calyx.

Fruit:
- *Form.*—Round. Seeds not protruding.
- *Surface.*—Smooth.
- *Color at maturity.*—Yellow.
- *Sepals.*—Permanent.

*Plant*

Form: Bush.

Growth: Very vigorous, upright, branching.

Foliage: Number of leaflets on normal mid-stem leaves 5.
- *Size.*—Large.
- *Quantity.*—Normal.
- *Color.*—New foliage: Slightly darker than Purple Madder (1028). Old foliage: Upper side slightly darker than Spinach Green (0960). Lower side lighter than Spinach Green (0960/3).

Leaflets:
- *Shape.*—Oval.
- *Texture.*—Leathery. Under side—smooth. Ribs and veins—ordinary.
- *Edge.*—Serrated.

*Serration.*—Single, small.

*Petiole.* — Rachis — color — green. Underside—prickles. Upperside has small prickles.

*Stipules.*—Medium.

*Disease resistance.*—Very resistant to mildew under normal growing conditions at Irvine, Calif.

Wood:

*New wood.*—Color—light green. Bark—smooth.

*Old wood.*—Color—close to Spinach Green (0960/3). Bark—smooth.

Thorns:

*Quantity.*—On main stalks from base—ordinary. On laterals from stalk—ordinary.

*Form.*—Medium base, hooked downward.

*Color when young.*—Light brown, tips much lighter.

*Position.*—Irregular.

Prickles:

*Quantity.*—On main stalks—few. On laterals—few.

*Color.*—Brown.

Short needles:

*Quantity.*—On main stalks—none. On laterals—none.

I claim:

1. A new and distinct variety of rose plant of the hybrid tea class, substantially as herein shown and described, characterized particularly as to novelty by the unique combinations of a tall, vigorous, well branched plant, freely borne flowers of Cardinal red aging to Rose Madder in color, and foliage extremely resistant to attack by rose powdery mildew.

No references cited.

ROBERT E. BAGWILL, Primary Examiner